United States Patent [19]

Kissel et al.

[11] Patent Number: 5,262,130
[45] Date of Patent: Nov. 16, 1993

[54] FIXED BED CHEMICAL REACTOR

[75] Inventors: Charles L. Kissel, Anaheim; Charles M. Finley, Arcadia, both of Calif.

[73] Assignee: Baker Hughes Inc., Houston, Tex.

[21] Appl. No.: 901,805

[22] Filed: Jun. 22, 1992

Related U.S. Application Data

[63] Continuation-in-part of Ser. No. 623,520, Dec. 7, 1990.

[51] Int. Cl.⁵ ............................................. B01J 35/02
[52] U.S. Cl. ................................ 422/311; 422/211; 422/221; 422/195
[58] Field of Search ............... 422/190, 191, 193, 195, 422/213, 221, 311; 568/479

[56] References Cited

U.S. PATENT DOCUMENTS

| | | | |
|---|---|---|---|
| 1,030,508 | 6/1912 | Eschellmann et al. | 422/195 |
| 1,636,685 | 7/1927 | Downs | 502/336 |
| 1,686,349 | 10/1928 | Slade | 422/218 |
| 2,443,423 | 6/1948 | Helmers | 422/211 |
| 2,930,184 | 3/1960 | Plescia et al. | 422/191 |
| 3,477,828 | 11/1969 | Schulze et al. | 422/221 |
| 3,595,626 | 7/1971 | Sowards | 422/211 |
| 3,628,314 | 12/1971 | McCarthy et al. | 422/218 |
| 3,732,078 | 5/1973 | Kassarjian | 422/191 |
| 3,838,977 | 10/1974 | Warren | 422/179 |
| 3,936,505 | 2/1976 | Oda et al. | 568/479 |
| 4,236,899 | 12/1980 | Gulden et al. | 48/89 |
| 4,276,265 | 6/1981 | Gillespie | 422/311 |
| 4,285,910 | 8/1981 | Kennedy, Jr. | 422/311 |
| 5,081,314 | 1/1992 | Kissel et al. | 568/479 |
| 5,143,847 | 9/1992 | Kawase et al. | 422/311 |

FOREIGN PATENT DOCUMENTS 963610 7/1964 United Kingdom ............... 568/479

*Primary Examiner*—Robert J. Warden
*Assistant Examiner*—Hien Tran
*Attorney, Agent, or Firm*—Rosenblatt & Assoc.

[57] ABSTRACT

A catalyst support for use in promoting oxidation reactions composed of metal particles is described. The metal particles are selected from the group of aluminum, tantalum, titanium, tungsten, niobium and mixtures thereof, where aluminum is preferred. The metal particles may have a rough diameter of from 0.02 to 10 mm. The particles may be in the form of spheres, shavings, irregular granules and the like. When the catalyst support is to be used in a tubular reactor, the ratio of the diameter of the reactor to the diameter of the catalyst may range from 1.1 to 200:1. The metal catalyst supports are inert in the reaction and give excellent uniformity in heat distribution throughout the catalyst bed. In oxidation reactions, the catalyst support may bear a metal oxide catalyst to give good results. The particulate catalyst support bearing the active catalyst may also be compressed to inhibit channelling and to help provide higher yield to the desired product. The use of perforated plates within the catalyst bed also aids heat distribution, prevention of channelling and product yield improvement.

16 Claims, 6 Drawing Sheets

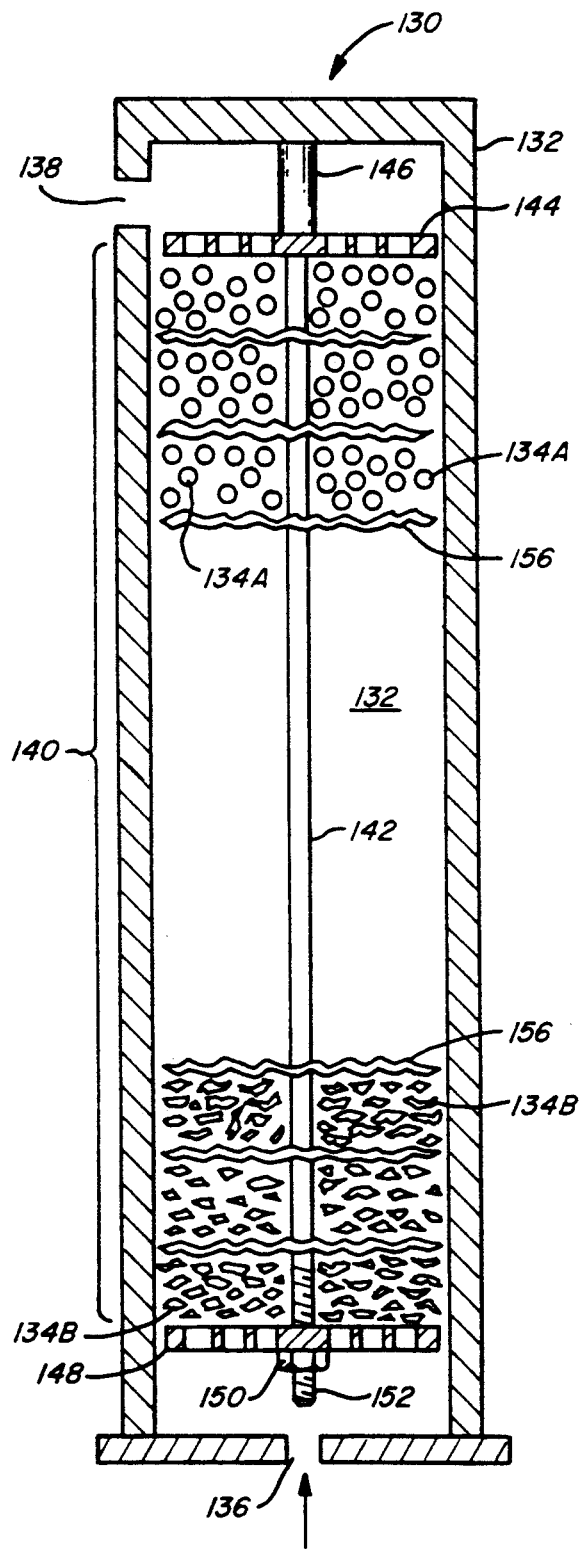
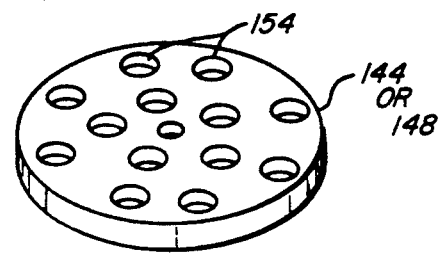
FIG. 7
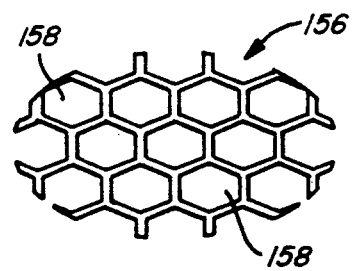
FIG. 8
FIG. 6

FIXED BED CHEMICAL REACTOR

CROSS-REFERENCE TO RELATED APPLICATION

This application is a continuation-in-part of U.S. patent application Ser. No. 07/623,520 filed Dec. 7, 1990, relating to catalyst supports for oxidation reactions.

FIELD OF THE INVENTION

The invention relates to catalyst supports, and more particularly, the invention relates, in one aspect, to catalyst supports for oxidation reactions and how they may be configured in a fixed bed chemical reactor.

BACKGROUND OF THE INVENTION

Catalyst supports are well known in the art. For example, various clays with high proportions of surface area to volume are known. Representative examples include montmorillonite clays, bentonite clays, Fuller's earth, kaolin clays, sepiolite clays, attapulgite clays, zeolites and mixtures thereof. Silica (sand) is also a commonly used catalyst support. Diatomaceous earth (diatomite; kieselguhr; infusorial earth) is also a common catalyst support. Ceramic-type materials, such as activated alumina, are also known as catalyst supports.

However, a common problem among conventional catalysts, whether used in fixed, fluidized or spouted beds, is that the heat distribution throughout the bed is poor, resulting in "hot spots" in the bed, which at a minimum degrade the product through unwanted side reactions and at worst cause runaway reactions with disastrous results.

Metals are known to provide better heat distribution through bodies of material, but metals are not used as catalyst support because they are also known to have catalytic activity themselves which can catalyze the reactants or products in undesirable side reactions. It is known to use metals themselves as catalysts without separate supports.

U.S. Pat. No. 1,636,685 teaches catalyst carriers having paticles of metallic iron coated with an iron aluminum alloy. Catalyst carriers of aluminum are mentioned as having been proposed but rejected in the prior endeavors.

The efficiency of fixed-bed catalytic chemical reactors usually depends on a variety of parameters, such as temperature, pressure, flow rate and the like, as well as the composition of the mixture of reactants which are fed to the reactor. In some instances, during the design and experimentation of the process, the efficiency of the reaction may still be improving when the practical limit of one or more of the parameters is reached. For example, during development it might be determined that it would have been desirable to make the reaction chambers larger in cross-section to increase the volumetric flow rate of gases through them. However, it may be discovered that larger chambers and flow rates result in disruption of the catalyst column in such a way that effective contact between the catalyst particles and the resulting gas mixture is lost. Movement of catalyst particles in response to the increased force of the gases pushing up on them may be sufficient to cause the catalyst column to "crack" vertically, forming a vertical channel in the direction of flow through which the gases are preferentially directed. Under these conditions, an abrupt drop in the efficiency of conversion of the reactants to product may occur, and the resulting yield of product may become low and unsatisfactory. Furthermore, once the channel has formed, the catalyst column cannot repair itself and can only be restored to its original efficiency by repacking.

A number of fixed bed structures are known. U.S. Pat. No. 3,595,626 notes that ceramic honeycomb placed within or on top of a packed bed, particularly a catalytic bed, improves the effectiveness of the bed. Such honeycomb structures may be fabricated by corrugating sheets of aluminum foil coated with fluxing agent and placing the corrugated sheets together node to node. Ceramic honeycombs dispersed throughout the bed were found to prevent plugging and/or channeling. The catalyst was loosely packed in the bed.

Checkerwork sections within a catalyst bed are used to heat the contents of the bed by induction according to U.S. Pat. No. 2,443,423. U.S. Pat. No. 1,686,349 teaches a process for conducting gaseous catalytic reactions and apparatus therefore which employs perforated partitions of heat insulating material transverse to the direction of flow. In both of these patents, the catalyst bed resided between the sections or partitions in loosely arranged form.

U.S. Pat. No. 1,030,508 describes a contact chamber with a catalyst bed portion having a plurality of perforated plates held at a distance apart from each other by distance pieces. The catalytic material was loosely packed on each plate.

A gas generator which comprises a heat resistant housing and a reaction chamber which is centrally arranged therein and contains a catalytic charge, with an inlet opening for the reactants and an outlet opening for the fuel gas is used for catalytically reacting liquid, hydrocarbon containing fuel to be evaporated with an oxygen containing gas at elevated temperature to form a fuel gas is described in U.S. Pat. No. 4,236,899. The housing of this generator consists of a lower part and a removable cover and the reaction chamber including the catalytic charge is replaceable. The fuel and/or the oxygen containing gas is fed to the reaction chamber for preheating and evaporating, respectively, via a system of tubes which is arranged between the reaction chamber and the lower part of the housing and is run around the reaction chamber in a helical fashion. The reaction chamber contains a packed bed with a plurality of plates having passage canals, the catalytic charge resting upon the plates.

It is known to oxidize propylene to acrolein using catalysts containing copper, bismuth, antimony, tin, molybdenum and mixtures thereof, particularly the oxides of these metals. Dilute solutions of acrolein are produced on site and on demand by oxidizing propylene in an improved reactor using an improved catalyst, which is a mixture of molybdenum, bismuth and tellurium oxides according to U.S. Pat. No. 5,081,314 to Charles L. Kissel and Charles M. Finley of CNC Development, Inc. The catalyst is deposited on metal particles, which are of a metal selected from the group consisting of aluminum, tantalum, titanium, tungsten, niobium and mixtures thereof, and are packed to form a catalyst bed which provides improved heat transfer and distribution for better control of the process. The reaction is conducted in a reactor in which all the exposed surfaces are made of a metal selected from the group just mentioned. The produced acrolein is absorbed to form a dilute solution of acrolein in a liquid to be treated, such as irrigation water for weed control, or control of hydrogen sulfide in water used for oil and gas field water floods, or in fuel oil to inhibit growth of organisms.

It would be desirable if further improvements could be made in the structure of fixed bed catalytic chemical reactors to prevent channeling in a simple manner.

SUMMARY OF THE INVENTION

Accordingly, it is an object of the present invention to provide a catalyst support useful in oxidation reactions which gives good temperature distribution throughout the catalyst bed.

It is another object of the present invention to provide a catalyst support which can be readily manufactured and which is relatively inexpensive.

Another object of the present invention is to provide a catalyst support for oxidation reactions which does not adversely affect the oxidation reaction or its reactants or products.

Yet another object of the invention is to provide a catalytic fixed bed chemical reactor which has a mechanism for inhibiting channeling from occurring.

Still another object of the present invention is to provide a fixed bed catalytic chemical reactor which has good temperature distribution and good reactant distribution throughout.

Another object of the invention is to provide a fixed bed catalytic chemical reactor which can be operated at low pressure and with low concerns about toxicity.

A final object of the invention is to provide a catalytic fixed bed chemical reaction which uses a support bearing a catalyst where there is good adhesion of the catalyst on the support.

In carrying out these and other objects of the invention, there is provided, in one form, a fixed bed catalytic chemical reactor having a reactor chamber for receiving a catalyst, the reaction chamber in turn having an inlet and an outlet. A catalyst bed comprising particulate catalyst is present within the reactor chamber. A mechanism for compressing the catalyst bed to inhibit movement of the catalyst within the bed is also present.

The catalyst is deposited on the supports of this invention, such as metal particles, such as spheres, shavings or the like. Depositing the catalyst on the metal particles improves temperature control and can significantly improve product yield.

A portable, self-contained system for generating dilute solutions of various products in significant quantities on-demand and on-site is ideal for use with the catalyst support of this invention, although it is expected that the catalyst support will find utility in other systems. With the portable system, the products are not produced and shipped in a concentrated liquid form, but instead are produced and used in a relatively short time on site in a dilute solution in a liquid compatible with the liquid to be treated.

A reactor using the catalyst supports of this invention can give a high yield of products from a reaction zone of about equal to or less than 18 inches long. Conventional prior art reactors are 10 to 30 times longer, making them impractical for use in portable units.

A preferred configuration of a reactor in which the catalyst support of this invention may be employed uses an air pump, if air is one of the reactants; a storage tank for another of the reactants, if appropriate; a pump for water or other liquid into which the product is to be dissolved or absorbed, if appropriate; a high-temperature reactor thermally insulated and suitably shaped (for example, substantially in the form of a cube) for minimum consumption and loss of energy; an absorber system to collect product, if gaseous, from the reactor and place it into a liquid at high efficiency; an exhaust gas purifier; and a control system using gauges, valves, sensors, and electrical circuits for positive, safe operation. The system can be sufficiently small to be mounted on a skid or a trailer, and only the reactants, the liquid and either electricity or fuel for an electrical generator are required to permit on-site and on-demand generation of the product dissolved in a flowing liquid stream. With this invention, there is no need to produce a concentrated liquid product, thus avoiding any inherent hazards that might be present with a product in that form.

BRIEF DESCRIPTION OF THE DRAWINGS

These and other aspects of the invention will be more fully understood from the following detailed description taken in conjunction with the accompanying drawings, in which:

FIG. 6 is a cross-section of one of the reaction chambers showing a plurality of perforated plates having catalyst therebetween which is compressed;

FIG. 7 is a three-quarters view of one of the end plates of the reactor chamber of FIG. 6;

FIG. 8 is a three-quarters view of one of the perforated plates of the reactor chamber of FIG. 6.

Figure 1:
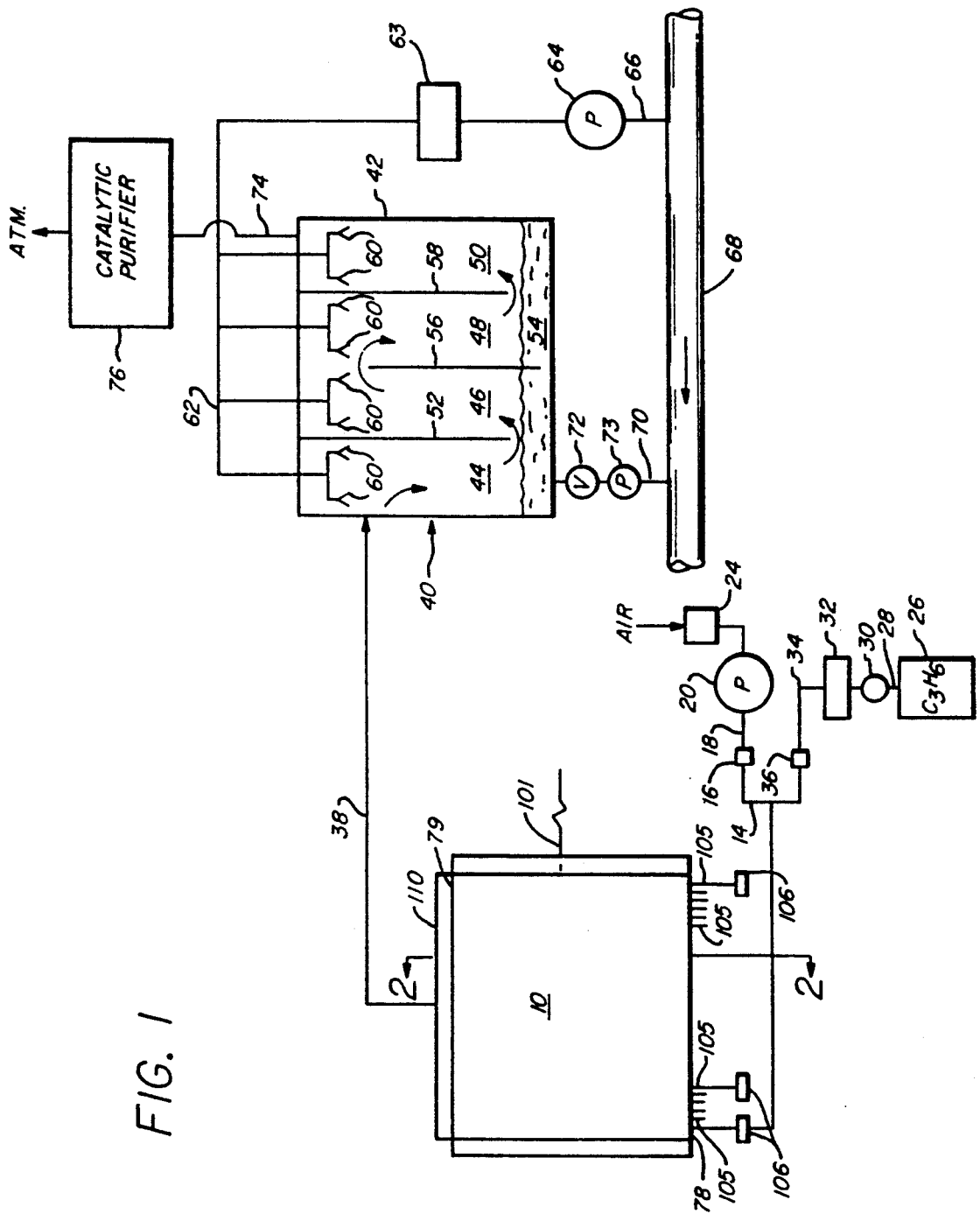
FIG. 1 schematically shows a reactor that may contain the catalyst support of this invention connected to receive a mixture of two gases, and to discharge the reaction products into an absorber.

It will be appreciated that the various elements depicted in the drawings are not necessarily to scale or proportion and that the invention is not limited to the particular configurations and designs portrayed.

DETAILED DESCRIPTION OF THE INVENTION

It has been discovered that in oxidation reactions that catalyst supports may be devised from materials heretofore believed unsuitable. It has been surprisingly found that metals and mixtures and alloys of metals of the group aluminum, tantalum, titanium, tungsten and niobium have been found to be useful. While these materials are known to have catalytic activity themselves in some contexts, in these oxidation reactions they are inert supports with the advantage of excellent temperature distribution throughout the catalyst bed.

The catalyst support has been actually used in conjunction with a relatively small, modular reactor, which may be easily moved from place to place to catalytically produce various chemical products. However, it will be appreciated that the catalyst support and method of compression of such support of this invention will find utility in other reactors and is not limited to the particular reactor system described in detail here. The reactor is an apparatus for making an organic product from at least two reactants, the apparatus having a catalyst chamber with an inlet and an outlet. A permeable bed of catalyst support of this invention may be in the. chamber between the inlet and the outlet, and a catalyst which promotes the reaction of the reactants to form the product is present on at least some of the support particles. A mechanism is provided for introducing the reactants through the inlet to the reaction chamber, and another mechanism is provided for removing the organic product from the reaction chamber through the outlet. Although it is conceivable that the catalyst support of the present invention may find utility in the production of inorganic materials, it is expected that it will find more applications in the manufacture of organic compounds, particularly those compounds produced in oxidation reactions.

As noted, the catalyst support of the present invention may be metal particles, where the metal particles are from the group of aluminum, tantalum, titanium, tungsten, niobium and mixtures thereof. The term "mixtures" as used herein includes alloys of the above-listed metals with each other as well as other ways in which the various suitable metals may be mixed, such as simply being blended or clad together or used physically adjacent to one another. Typically, the particles may be from about 0.02 to 10 mm in characteristic dimension, and preferably from about 2.0 to 8.0 mm in characteristic dimension. This latter range corresponds to a mesh size of from about 60 to about 8. A preferred mesh size ranges from about 40 to about 8. The ratio of the reaction chamber diameter to the catalyst support characteristic dimension may range from about 1:1 to 200:1, and preferably from about 1.5 to about 10.0:1. The term "characteristic dimension" is used to denote a common dimension for the particular shape, where the dimension is used to indicate its size. For example, for a sphere, the characteristic dimension is the diameter, for a cube, the characteristic dimension would be the length of one side, etc.

The catalyst is provided on the particles in a uniform, adherent coating. In one embodiment for oxidation reactions, the catalyst is a metal oxide or a mixture of metal oxides. The resultant material does not clump together, nor does the catalyst become powdery and fall away from the aluminum particles during mixing or loading into the reaction chambers of the reactor. Aluminum is a preferred support in some embodiments. Other metal particles can also be used as a catalyst support, as long as the metal has good thermal conductivity, and does not adversely affect the production of acrolein. The catalyst support particles need not be perfect spheres, but can be granular and in other irregular shapes, such as pieces of metal shavings, saddles, rings and the like. In one embodiment of the invention, the metal support particles may be deformable, that is, they may be of a shape or flexibility that when compressed give or deform at least slightly. While spheres deform to a slight extent, shapes which are more deformable include, but are not limited to, flakes, shavings, rings, cubes, prisms, pyramids, cylinders, plates, discs, helices, Intalox TM and saddles, for example. Intalox TM is a trademark for a particular shape of catalyst support available from Norton Company, Metals Division. Such shapes are preferred embodiments of the invention. Fabrication of the metal supports can be accomplished by any readily available and suitable metal production or machining process.

An apparatus capable of serving as the reaction chamber for the catalyst support can have various shapes, such as cylindrical or rectangular blocks, each containing hollow passageways capable of containing the catalyst and the reaction. These passageways may be tubular in nature, or they may be configured as to form a fixed-bed chamber, or numerous single tubes can be assembled in various arrays. Spouted beds or fluidized reactor zones could also be used. Though these later reaction chamber types have inefficient temperature/heating characteristics, the catalyst support of this invention will help improve those characteristics.

One apparatus for making acrolein includes a reactor as described above with at least one pair of substantially parallel plates disposed side-by-side. Each plate includes catalyst or reaction chambers which each have a respective inlet and outlet. A catalyst on the catalyst support of this invention in each chamber promotes the reaction, for example, the oxidation of propylene to acrolein, and a mechanism is provided for introducing the reactants, such as a mixture of propylene and oxygen, into the catalyst chambers through the inlets. A heating element or panel between the plates heats the reactants and the catalyst to a temperature which causes the reactants to react with each other in the presence of the catalyst on the support to form the reaction products. A mechanism is also provided for removing the reaction products from the outlets of the catalyst chambers.

In one configuration of this reactor, each plate is in the shape of a rectangular slab having major sides many times greater than the thickness of the slab. The slab has a first minor end and a second minor end opposite the first minor end. For example, each plate may be a rectangular slab about 1" thick, with opposing major faces each being approximately square and having a dimension of about 18" on each side. A plurality of elongated and laterally spaced bores extend through each plate in a direction substantially parallel to the major faces of the plate beginning at the first minor end and terminating at the second minor end, to provide as many as 20 to 30 parallel catalyst chambers in each plate. The reaction chambers may be said to extend from one minor end to an opposing minor end on opposite sides of the plate, beginning at one end with their inlet and terminating at the other with their outlet.

A thin, panel-shaped flat heating element may be sandwiched between adjacent major faces of a pair of plates to form a heated pair, or cell, the temperature of which is controlled by a thermostat mounted in a face of one of the plates adjacent the heating element. Preferably, heat insulation around the assembled plates which form the reactor limits the amount of external energy which must be applied to the apparatus. A separate respective capillary tube is connected at one end to a respective catalyst or reaction chamber inlet, and at the other end to a reactant supply pipe, which supplies a mixture of reactants to each catalyst chamber inlet through a respective capillary tube. These capillary tubes are fed by a common header containing pressurized mixed starting materials. This arrangement uses frictional drag in the tubes to control the flow rates through each of the separate reaction chambers. Although capillaries are preferred for flow control, other devices, such as orifices or adjustable valves, may also be used.

A separate elongated collection header over the outlets of the catalyst chambers in each plate collects reaction products leaving the reaction chambers. Each of the catalyst chambers is packed with a bed of catalyst on the catalyst support of the invention, which catalyst preferentially promotes the reaction, such as the oxidation of propylene to acrolein.

An embodiment of the reactor system includes a plurality of pairs of parallel plates, each pair being constructed and arranged with a panel-shaped heating element as described above. A sufficient number of the pairs of plates are staked together to form an array, or a reactor, essentially in the shape of a cube to mininmize heat loss. In another embodiment, the plates could be curved or flat and arranged concentrically. The space between adjacent pairs of plates is thermally insulated to provide good temperature control in each pair of plates served by a respective panal-shaped heating element.

Preferably, the plates are made of a metal selected from the group of aluminum, tantalum, titanium, tungstein, niobium or mixtures thereof, or at least the inner surfaces of the reaction chambers are made from these metals. It is additionally preferred that all internal surfaces contacted by the gases and/or liquids passing through the catalyst chambers and collection headers, absorber, if present, and conduits connecting the headers and absorbers or other pieces of equipment are made of metals selected from that group. It is possible that some tubing and conduits not subject to high temperatures or other parameters, e.g. pressure, may be made from inert polymeric plastics, elastomers and the like, provided they meet the safety criteria.

Suitabl mechanisms are provided for sensing the temperature of the catalyst and controlling the heat supplied by the heaters to keep the catalyst temperature within its operating range. Of course, if the expected reaction temperature range exceeds the softening point of the metal used to line the reaction chambers, for example of aluminum, one should plan to use a different material selected from the above-enumerated list.

The system also includes a pump for taking a stream of liquid from a source of liquid which is to be treated with the reaction product. Spray nozzles connected to the pump outlet, or other source of liquid under pressure, spray liquid into an absorber, through which the reaction products from the catalyst chambers pass. The reaction product is absorbed in the liquid stream from the liquid supply, and added to the system to be treated, or undiluted if the system to be treated is composed wholly of the product stream from the reactor. If gases are a product, those which are not absorbed in the liquid sprayed into the absorber pass through a catalytic purifier.

The catalyst support of the invention has been successfully used to catalytically produce (1) acrolein from air and propylene; (2) methacrolein from isobutylene and air; and (3) acrylonitrile from propylene and ammonia. The example of making acrolein from propylene and air will be used from time to time throughout this description as representative of an actual use of the catalyst support, but the invention should not be limited to only this example.

Referring to FIG. 1, a reactor 10 in the general shape of a cube receives a gas mixture of air, as a reactant, and propylene, as the other reactant, from a plurality of horizontal and parallel supply lines 12 (see FIG. 2), each connected at respective inlet ends through a respective T-joint 14 to the discharge of a respective air pressure regulator 16, the inlet of which is connected by an air manifold line 18 to the discharge of air pump 20 having an inlet 22 connected to a filter 24, through which air is drawn.

A tank of one of the reactants, propylene for example, has a discharge line 28 connected through a primary pressure regulator 30 and a filter 32 to a gas supply line 34 connected through a secondary pressure regulator 36 to the T-joint 14. Obviously, if liquid reactants are used, these gaseous sub-system would be replaced by the liquid tanks, supply lines, pumps, etc.

Reaction products from the upper side of the reactor are carried by a delivery pipe 38 (see FIG. 1) to an absorber 40, which includes a housing 42 divided into first, second, third, and fourth absorption zones 44, 46, 48 and 50, respectively. A first vertical baffle 52 extends from the top of the housing 42 downwardly to terminate just above a pool 54 of liquid, which may be water, fuel, or other liquid which absorbs acrolein. A second vertical baffle 56 mounted in the housing parallel to, and spaced horizontally from, the first baffle extends from below the level of liquid pool 54 and a short distance below the top of the housing. A third vertical baffle 58 parallel to, and spaced from, the second baffle extends from the top of the housing down to terminate just above the surface of the liquid pool 54. Each of the baffles extends entirely across the housing in a direction perpendicular to the plane of FIG. 1 so that the three baffles divide the housing 42 into the four absorption zones 44, 46, 48 and 50.

A separate respective group of spray nozzles 60 mounted in the upper end of each absorption zone are supplied liquid from a liquid supply pipe 62 connected through a pressure regulator 63 to the discharge of a pump 64, which has as its inlet connected through a suction pipe 66 to a main body or stream of liquid flowing a main pipe 68. Line 66 and pump 64 may be replaced by other suitable sources, such as pressurized water lines typical of fire hydrants and hose bib stand pipes. In any event, the pressure of the incoming fluid is determined by a pressure regulator 63, or other suitable flow-monitoring device.

A drain pipe 70 extands from the liquid pool 54 in the housing through a control valve 72 and a return pump 73 to return product-containing liquid in the absorber to the main pipe 68. Alternatively, the product-containing liquid may be sent to storage for future use.

An exhaust conduit 74 carries unabsorbed gases from the upper end of the fourth absorption zone 50 to a catalytic purifier 76, which oxidizes the remaining hydrocarbons and any carbon monoxide to water and carbon dioxide, which are discharged to the atmosphere.

Figure 2:
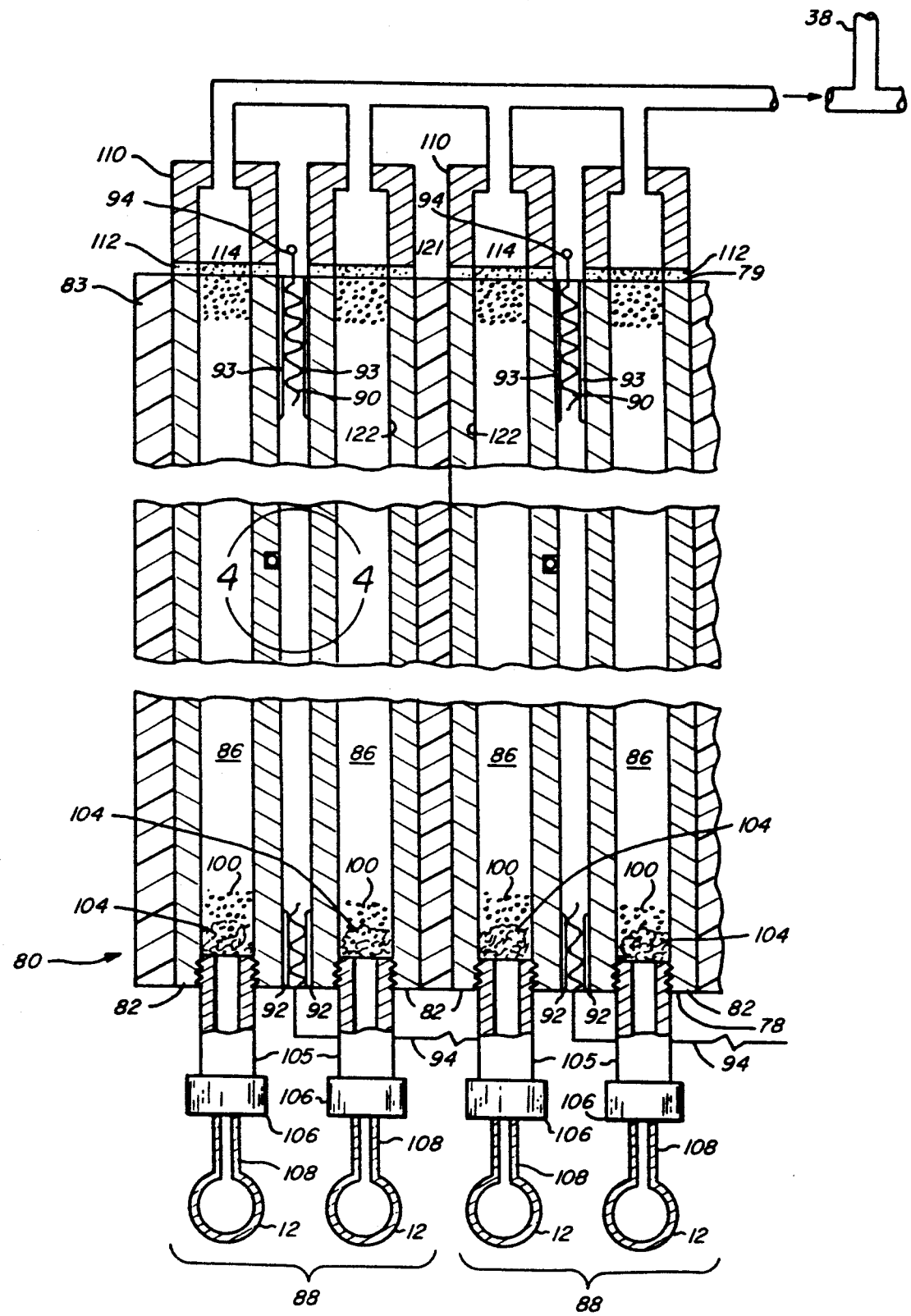
FIG. 2 is a view taken on line 2—2 of FIG. 1 showing details of the reactor in cross-section.

As shown in FIG. 2, the reactor 10 may be a sandwich assembly or array 80 of a plurality of flat, rectangular plates or slabs 82 disposed side-by-side so the reactor is substantially in the shapoe of a cube to minimze heat loss from a given volume for the reactor. A layer 83 thermal insulating material surrounds the reactor to reduce heat loss and energy consumption. Each plate 82 has a first minor end 78 containing the inlets to the reactor plate, and a second minor end 79 opposite the first minor end containing the outlets. First minor end 78 and second minor end 79 are generally perpendicular to the major face of slab 82.

Figure 3:
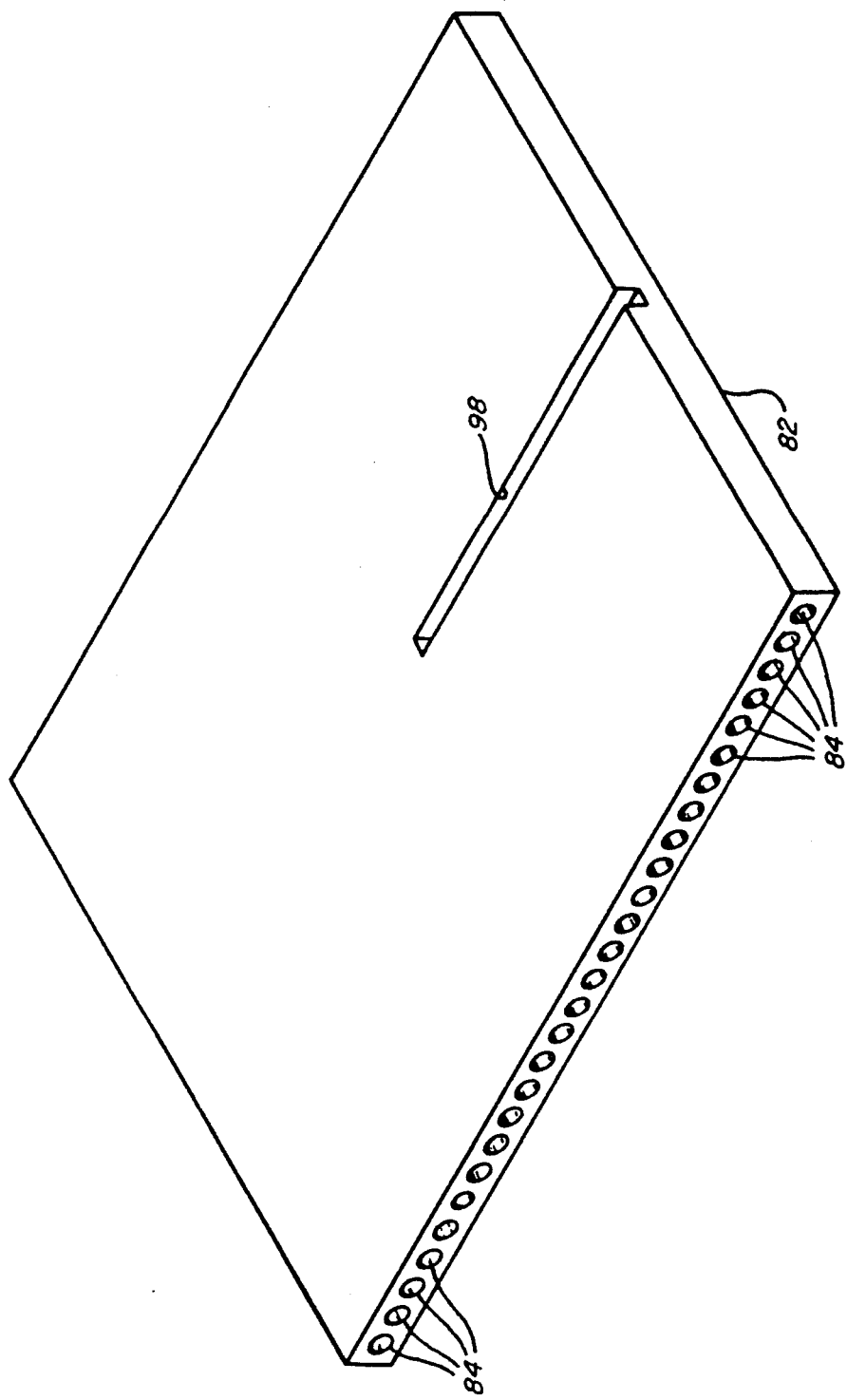
FIG. 3 is a perspective view of one of the parallel plates in the reactor.

Although the plates may be of any suitable dimensions, a successful reactor has been designed in which the plates are about $18'' \times 18'' \times 1''$. The plates are assembled with their major surfaces vertically oriented to form the assembly each plate. If the plate is about 1" thick, it has been found that bores about ½" in diameter, and located on about ⅝" centers form properly spaced and dimensioned reaction chambers 86 (FIG. 2). The bores 84 need not have a circular cross-section, as shown in FIG. 3. For example, the bore which defines the interior shape of the reactor chamber 86 may be a single bore, rather than a plurality, and may have other cross-sectional shapes, a reactor with a single catalyst bed 2" thick by 18" wide by 20" long may be employed.

Figure 5:
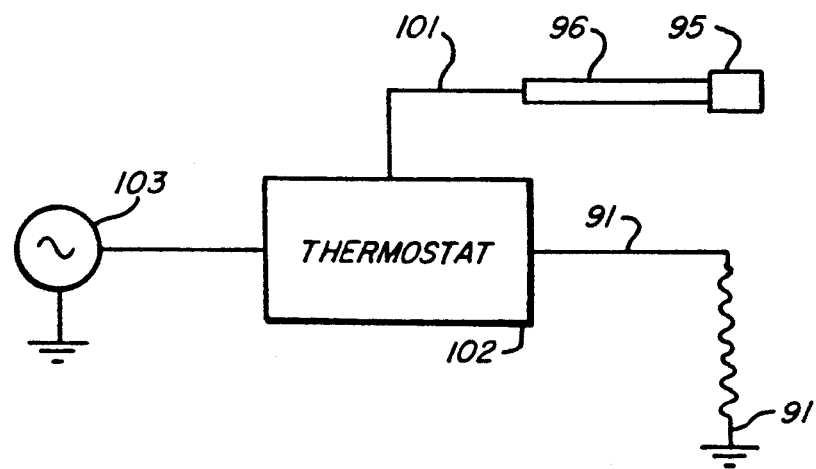
FIG. 5 is a schematic diagram showing a circuit for controlling the temperature of the catalyst in the reactor.

The plates may be arranged in pairs 88 (FIG. 2), with a separate, respective, flat electrical heating panel 90 disposed between adjacent faces 92 of each plate in each pair. A thin, separate, respective sheet 93 of ceramic insulation is between each face of each electric panel and the adjacent face of a plate. The thin sheet of ceramic insulation, which can be of any suitable thickness, say 0.03 to 0.07", provides a more uniform transfer of heat from the electric heating panels 90 to the entire adjacent surfaces of the plates. Electrical power leads 94 (FIGS. 2 and 5) supply power to the heater panels.

Figure 4:
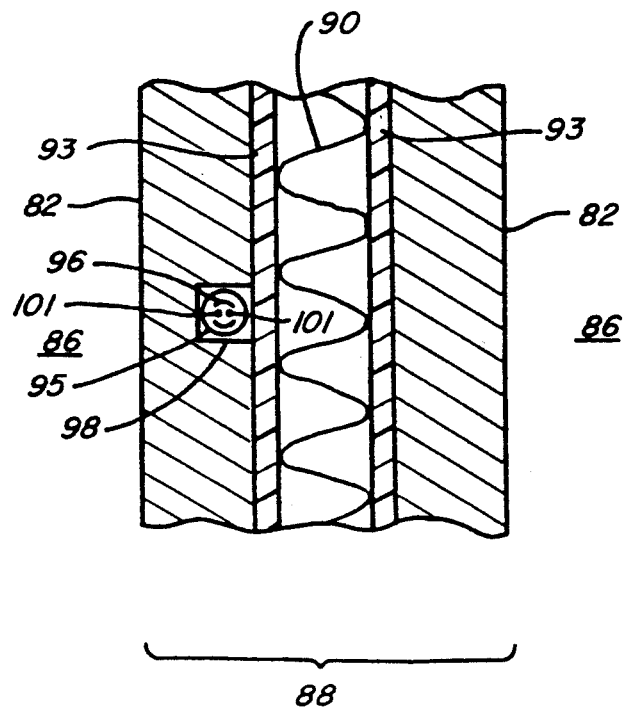
FIG. 4 is an enlarged view taken in the area 4—4 of FIG. 2.

A thermocouple 95 on the inner end of a horizontal support 96 (FIGS. 4 and 5) in a horizontal groove 98 extending from about the center of one vertical edge of a plate in each pair to about the center of that plate, and opening toward the other plate in the pair, senses the temperature of the plates surrounding the respective reaction chambers 86, each of which is filled with a bed 100 of a catalyst which promotes the reaction upon the catalyst support of this invention. In this particular non-limiting example, the catalyst was a metal oxide catalyst. A separate pair of electrical signal leads 101 (see FIGS. 4 and 5) extend from each respective thermocouple to a respective adjustable thermostat 102, which controls the amount of electrical power supplied from a generator 103 to a respective electrical heater panel 90 to keep the catalyst in the adjacent reaction chamber 86 at the required operating temperature.

A separate, respective loose plug 104 (FIG. 2) of quartz wool in the bottom of each reaction chamber 86 rests on the upper end of a separate, respective short nipple 105 threaded into the lower end of a respective reaction chamber to form a reaction chamber inlet. A separate, respective capillary tube 108 is sealed at its lower end to a respective gas supply pipe 12. The capillary tubes act as a flow control devices may be of any suitable internal diameter for that purpose. Capillary tubes with an inside diamter of about 0.007" provide good flow control and distribution of reactant gas from the supply pipes 12.

A separate, elongated, rectangular header 110 rests on a separate, respective graphite gasket 112 on the upper edge of each plate and over the upper (outlet) ends of the reaction chamber in each plate to collect reaction products which flow up through the reaction chambers, through respective holes 114 in the gasket 112, and to the delivery pipe 38 (see FIGS. 1 and 2).

The reactor plates and all other components with surfaces contacted by the reaction products should be made of a material which has good thermal conductivity, and which does not adversely affect the production of the desired product. For example, to provide acrolein by oxidizing propylene, aluminum is preferred because of its relatively low cost. Other metals, such as tantalum, titanium, tungstein, niobium or mixtures of these, may also be used. Aluminum alloys of the 6000-type are preferred because they are inert, machinable, and can be welded. These are unusual materials for reactors, but have been found to be particularly advantageous for catalytic oxidation reactions. These metals are the same as those found useful for the catalyst support of this invention. The use of ferrous metals within the reactor decreases the selectivity of the process to acrolein, if that is the reaction run. Brass, bronze and copper are also not used becausr they deteriorate chemically when contacted with such reactants as air and propylene. Similarly, these metals are not desired for the catalyst support. We are not aware of any prior art use of aluminum equipment, except for the single report of the use of aluminum tubes that were coated with copper as a catalyst described by Xing and Inoue, *Kagaku Kogaku Ronbunshu*, Vol. 10, No. 4, p. 439–45 (1984).

A separate respective panel 121 of thermal insulation between the adjacent outer faces 122 of each adjacent pair of plates provides good temperature control for each pair of plates served by a respective heating panel 90. The panels may be of any suitable material, such as sandstone, refractory material, spun glass, and the like. Each panel has sufficient thickness to reduce thermal flow between reactor pairs 88. Although asbestos, asbestos-filled materials such as magnesia, and transite can provide adequate protection against thermal convention, their use is discouraged due to possible environmental health hazards.

Each reaction chamber was filled with a mixture of aluminum support particles coated with catalyst to provide the catalyst bed. The catalyst/aluminum mixtures seem to give better yields and fewer side products, probably because the high thermal conductivity of the aluminum particles ensures substantially uniform temperature throughout the catalyst bed.

The operation of the reactor will now be described using the production of acrolein as illustrative only of an actual use of the catalyst support of the invention. With the reactor packed with beds of supported catalyst, as described above and shown in FIG. 2, a mixture of air and propylene in a ratio of 84:16, respectively, by volume, was fed into the inlets of the reaction chambers, which were heated to about 410° C. The pressure in the reaction chambers was between about 2 and about 5 lbs./in.$^2$, and the flow rate per unit of cross-sectional area was about 100 ml/min./cm$^2$. The effluent from the reaction chambers 86 flowed through the aluminum headers and the aluminum delivery pipe 38, which were surrounded by a layer of insulation (not shown) to keep the gas in them at a temperature above about 60° C. to prevent premature condensation of acrolein, and into the upper end of the first absorption zone of the absorber. The effluent was contacted in the first absorber zone by a spray of water supplied by pump 64 to the spray nozzles. The intake of the pump was connected to main pipe 68 carrying a main stream of water to be treated with acrolein. Water droplets with absorbed acrolein fell into the pool 54 in the bottom of the absorber. Unabsorbed gases passed under the first baffle 52 and into the bottom of the second absorption zone following the arrows shown in FIG. 1, rising to meet more water droplets sprayed into the top of that zone. Additional acrolein was absorbed and carried to the pool in the bottom of the absorber. The unabsorbed gases continued over the top of the second baffle into the top of the third absorption zone for additional absorption of acrolein, and passed under the third baffle to flow up through the spray of water in the fourth absorption zone, and out the exhaust conduit 74 through the catalytic purifier 76.

The water sprayed into the absorber scrubbed more than 99.9% of the acrolein from the reactor effluent, and carried it into the liquid pool in the bottom of the absorber, where the acrolein-rich water was removed through the drainpipe 70 and returned to the main stream of water downstream of the pump inlet.

In the example just described, the concentration of the acrolein in the water pool in the bottom of the absorber was about 0.2%, by weight, and it was returned to the main water stream at a rate to give a treated solution with between about 1 and about 15 ppm acrolein for weed control in ditches through which the treated water flowed. Approximately the same concentration would be used for treating injection wells for secondary recovery of oil.

The acrolein added to water for secondary recovery can scavenge hydrogen sulfide ($H_2S$) and destroy microbes (e.g., anaerobic bacteria which consume sulfur, say from calcium sulfate which may be available in the injection water or in the formation, and convert it to $H_2S$, a corrosive compound), which may be in either the treated water, or downhole, or both. In either case, the reactive nature of the acrolein in the dilute solution causes the acrolein to substantially disappear within a few days. It is possible to operate the absorber to produce a solution which contains up to about 25% acrolein by weight.

The invention will now be described further with respect to FIGS. 6-8. FIG. 6 shows a fixed bed catalytic chemical reactor 130 having a reactor chamber 132 for receiving a catalyst 134, where the reactor chamber 132 has an inlet 136 and an outlet 138. A catalyst bed 140 within the reactor chamber 132 has particulate catalyst 134. The particulate catalyst 134A shown in the top portion of the reactor chamber 132 is of spherical shape, whereas the particulate catalyst 134B illustrated in the bottom portion of the chamber 132 in FIG. 6 has a flake-like shape. The use of two different catalyst shapes 134A and 134B is merely illustrative and not meant to suggest using different shapes in the same reactor. While not limited to only one shape of catalyst or catalyst support, it is anticipated that the invention would be practiced with only one catalyst support shape.

In the embodiment shown in FIG. 6, there is present a mechanism for compressing or deforming the catalyst. In the particular, non-limiting mechanism shown, a central rod 142 is present having a fixed end plate 144 spaced apart from the top of the reactor chamber 132 by a spacer 146. On the other end of the central rod 142 is a movable end plate 148 adapted to have its position adjusted by a movable mechanism such as loading nut 150 riding on threads 152. Tightening loading nut 150 on threads 152 of rod 142 urges movable plate 148 toward fixed end plate 144 thereby compressing the catalyst 134 between them. Fixed end plate 144 and movable end plate 148 may have essentially identical design as shown in FIG. 7, with the exception that fixed end plate 144 is adapted to be fixed in position, while movable end plate 148 is adapted to ride freely on rod 142.

Both fixed end plate 144 and movable end plate 148 must be perforated with at least one perforation 154. It will be appreciated that the perforations need not be circular in shape, nor in the positions or in the numbers shown in FIG. 7. While plates 144 and 148 should not have perforations 154 so large as to permit particulate catalyst 134 to pass therethrough, the plates 144 and 148 should not appreciably block the products or reactants from passing therethrough.

It will also be appreciated that the compression or deformation mechanism illustrated in FIG. 6 is only one of many that may be employed. For example, it is possible to imagine a design where one or both of the end plates 144 or 148 is eliminated and perhaps the chamber 132 telescopes. Alternatively, one end plate 144 may be fixed while the movable end plate 148 is moved toward it by a mechanism at its near end of the chamber 132, rather than by riding on a rod extending the length of the chamber 132 from its far end.

The inventors found that the formation of channels through the catalyst bed resulted in an abrupt drop in efficiency of the conversion of the reactants, for example, an air-propylene mixture to acrolein, as described above. It was discovered however, that if the column of catalyst or catalyst bed was mechanically restrained in its movement in any direction, longitudinally with the flow stream of reactants/products and laterally or transversely (sideways) that channeling could be inhibited. The result was that the catalyst bed could be used longer without repacking. In one embodiment of the invention, the catalyst bed is compressed at least about 2% and preferably at least about 5% from its initial packed, but uncompressed position. In another embodiment, the bed is compressed at least about 10%. The invention will be illustrated further with respect to the following Examples, which are merely illustrative and are not limiting of the invention.

EXAMPLE 1

A test reactor having a 2.5 inch diameter bore, was set up and tested, as illustrated in FIG. 6. A mechanism such as that shown was provided whereby the catalyst column could be compressed lengthwise by a known amount. The catalyst column or bed, some 14 inches in length before compression, was loaded into the reactor along with approximately 40 perforated aluminum plates of 2.5 inches in diameter, one plate being installed at approximately every 0.33 inch of catalyst column length.

These plates were made of expanded metal and are illustrated in FIG. 8 as perforated plates 156. Perforated plates 156 need not have the exact shape shown in FIG. 8, which is merely illustrative and perforations therein 158 need not be hexagonal; indeed, perforated plates 156 may be of the design of end plates 144 and/or 148, shown in FIG. 7 or other design. In one embodiment of the invention, each plate 156 has at least 10 area percent of the plate surface open, an intermediate range of about 20-40 area percent is preferred and most preferably at least 75 area percent of the plate surface open. The perforated plates 156 are oriented approximately parallel to the cross-section of the reactor chamber 132 and the direction of flow of reactants/products is normal to the cross-section of the chamber 132.

The purpose of the perforated plates 156 was twofold: (1) to ensure good heat transfer from the central regions of the reactor chamber 132 to the walls so that the catalyst bed would be homogeneous in temperature, and (2) to trap the catalyst particles and their substrate (support) of coarse aluminum granules so that sideways or lateral movement would be minimized when the catalyst column was compressed mechanically along its length. It was desirable to compress the catalyst bed 140 easily along its long axis, but not to spread laterally during the "compression" phase of the assembly.

The perforated plates 156 were also discovered to be an important part of the invention. Their inclusion resulted in a far more uniform distribution of gas throughout the large diameter column of catalyst and also apparently caused the compressive force to spread uniformly through the mass of catalyst. The perforated plates 156 may be made of any of the metals mentioned earlier as having good heat transfer properties: aluminum, tantalum, titanium, tungsten, niobium and mixtures thereof.

The first tests of the 2.5 inch inner diameter (I.D.) reactor gave excellent results: good acrolein yields, the ability of the reactor to maintain high yields even at much increased flow rates, and further no observed channeling at any flow rate tested.

The original 0.5 in. diameter tubes first employed had been limited to a throughput of about 650 cc/min./in.$^2$ and further, absolutely limited to 0.5 in. as a maximum diameter. If the use of diameters over 0.5 in. was attempted the throughput values diminished and frequently channeling occurred so that no net improvement could be obtained. By contrast, the new, larger-diameter reactor with the perforated plates and compression easily operated at throughputs as much as three times the small-bore tube limit of 650 cc/min./in.$^2$. Flow rates as high as 10,000 cc/min. (10 liters/min.) were passed through the large bore reactor in tests; acrolein yields were very good and no evidence of channeling was observed. Since the cross-sectional area of the large-bore reactor was 4.9 in.$^2$, such a flow rate corresponded to a throughput of over 2,000 cc/min.-/in.$^2$.

The development of the fixed bed catalytic chemical reactor has been greatly helped by this improvement, since a larger reactor chamber may be used and significant cost reductions may be realized due to the simplification of the reactor and all of the reactant and product handling components.

Subsequent to the first tests, described above in Example 1, the large-bore reactor was emptied and packed with new catalyst several times. At first, in an attempt at further simplification, the perforated plates were left out, because it was thought that their contribution to the overall result might be trivial. The consequences of this modification were very unsatisfactory. Some areas of the catalyst bed in the reactor seemed to compress while others did not, resulting in places through which gas apparently passed very slowly as well as places where it passed very rapidly. Conversion efficiency and yield were poor, and undesirable side products of the reaction increased, apparently due to excessive contact time between air, propylene and catalyst in some regions. Some parts of the catalyst bed turned black from decomposed organic materials which had burned to tar or carbon. Additionally, catalyst activity generally declined over time.

EXAMPLES 2-3

In these Examples, the reactor tube is 0.5" I.D.×13" long stainless tube having an internal volume of 36 ml, and operated with a feed supply of 100 ml/min. of air and 10 ml/min. propylene, as measured with rotometers. Sieved aluminum flakes were charged into the stainless tube, and the weight of the flakes was noted. The inlet head pressure was noted for the above specified flow rate (combined air and propylene) at both 20° C. and 400° C. Afterwards, the pore volume was determined by measuring the weight of acetone used to fill the packed tube and correcting for the density of acetone to yield volume. Results are shown in Table I.

TABLE I

| | Pressure and Voidance Results Using Flake Catalyst Support | | | |
|---|---|---|---|---|
| | Mesh of | Flake | Head Pressure, psig. | Voidance, |
| Ex. | flake | wt., g. | 20° C. | 400° C. | ml |
| 2 | 10/16 | 9.8 | 0.4 | 0.41 | 32.4 |
| 3 | 16/20 | 10.2 | 0.43 | 0.46 | 32.2 |

These data suggest the packed tube has a great deal of voidance (32 ml of the total available 35 ml), leaving the mass of aluminum to occupy a small volume, about 3.7 ml, which is in close agreement with the calculated value based on aluminum's density of 2.702 g/ml. The preferred characteristics are low aluminum mass (catalyst support) with high voidance, for a completely packed tube. In one embodiment of the invention, the voidance present with the catalyst support with active catalyst thereon (explored below) should be at least about 10%, preferably at least about 15% and most preferably at least about 25%. In one embodiment, the voidance may be between about 50 and 70%.

EXAMPLES 4-8

These Examples are the same as 2-3 above, except that aluminum shot replaces the flaked catalyst support material. The data are presented in Table II.

TABLE II

| | Pressure and Voidance Results Using Spherical Shot Catalyst Support | | | | |
|---|---|---|---|---|---|
| | Mesh of | Flake | Head Pressure, psig. | | Voidance, |
| Ex. | flake | wt., g. | 20° C. | 400° C. | ml |
| 4 | 8/10 | 61.3 | 0.3 | 0.32 | 13.3 |
| 5 | 10/16 | 59.1 | 0.4 | 0.41 | 14.0 |
| 6 | 16/20 | 57.1 | 0.41 | 0.45 | 14.9 |
| 7 | 20/40 | 54.0 | 0.45 | 0.54 | 16.0 |
| 8 | 40/60 | 28.8 | 0.52 | 0.78 | 25.5 |

In Examples 4-8, the mass of shot occupies a larger volume of the packed tube and the voidance is decreased. As the shot size decreases (with increasing mesh number), the pressure at the inlet/head increases. It is not possible to achieve low head pressure while maintaining low aluminum mass with high voidance when shot is used. Also note that head pressure differences between 20° and 400° C. are larger for the smaller size shot.

EXAMPLES 9-11

These Examples are the same as 2-8 above, except that commercial aluminum shot of the following size distributions were used. The data are presented in Table III.

| | Percentage of shot at Mesh range | | | | | |
|---|---|---|---|---|---|---|
| Shot supplier | 4/8 | 8/10 | 10/16 | 16/20 | 20/40 | 40/60 |
| Noah | — | — | 4.6 | 62.2 | 33.1 | 0.1 |
| Reynolds | 35.8 | 22.5 | 40.5 | 0.1 | 0.1 | — |
| Kaiser | 85.8 | 9.7 | 4.5 | — | — | — |

TABLE III

Pressure and Voidance Results Using Commercial Shot Catalyst Support

| Ex. | Mesh of flake | Flake wt., g. | Head Pressure, psig. 20° C. | Head Pressure, psig. 400° C. | Voidance, ml |
|---|---|---|---|---|---|
| 9 | 10/60 (Noah) | 59.3 | 0.43 | 0.49 | 14.0 |
| 10 | 4/40 (Reynolds) | 58.7 | 0.3 | 0.33 | 14.1 |
| 11 | 4/16 (Kaiser) | 66.3 | 0.3 | 0.31 | 11.6 |

Again, larger size shot means lower voidance when considering wide shot size distributions. The most preferred conditions cannot be met even with blends of different shot sizes.

EXAMPLES 12-22

These Examples use the same procedures as in Examples 2-11 above, except that Bi-Mo-Te-O catalyst is admixed with the aluminum support using 40 g catalyst and 60 g support for each admixture as a stock to fill each tube. The catalyst is characterized as 65% 40/60 mesh, 20% 60/80 mesh and 15% 80/200 mesh with a density of 1.22 g/ml. The results are presented in Table IV.

TABLE IV

Pressure and Voidance Results Using Supports With Catalyst

| Ex. | Mesh of particle | Particle wt., g. | Head Pressure, psig. 20° C. | Head Pressure, psig. 400° C. | Voidance, ml |
|---|---|---|---|---|---|
| 12 | 8/10 shot | 68.1 | 1.1 | 1.5 | 9.9 |
| 13 | 10/16 shot | 67.6 | 0.7 | 1.0 | 9.6 |
| 14 | 16/20 shot | 66.1 | 0.7 | 1.2 | 9.2 |
| 15 | 20/40 shot | 46.4 | 0.85 | 1.45 | 9.1 |
| 16 | 40/60 shot | 28.3 | 0.98 | 1.6 | 22.1 |
| 17 | 10/60 Noah | 58.8 | 0.77 | 1.2 | 8.4 |
| 18 | 4/40 Reynolds | 58.2 | 0.7 | 0.9 | 8.6 |
| 19 | 4/16 Kaiser | 64.8 | 1.2 | 1.7 | 8.8 |
| 20 | 10/16 flake | 20.1 | 0.45 | 0.53 | 18.3 |
| 21 | 16/20 flake | 20.8 | 0.47 | 0.55 | 19.1 |
| 22 | 100% catalyst without support | 32.2 | 8.6 | 16.5 | 9.4 |

Admixing catalyst with aluminum support still produces low masses in the packed column tube with high voidance and low head inlet pressures when flake is used as compared with shot. Higher pressures at 400° C. when compared to 20° C. again increases as the shot or flake size decreases, and this increased pressure is the result of both the aluminum and the catalyst expansions.

The higher pressure for the 8/10 shot support is the result of the poor adhesion of catalyst to the shot, which caused catalyst plugs to form in the pores of the admixture. Smaller size aluminum/catalyst systems were found to produce hot spots and charring upon examination after the runs, especially true in the 40/60 shot and the Noah runs. Example 22 (neat catalyst) produced a hot spot which caused the tube to glow cherry red; much char was observed in the system after the run.

In all shot cases, catalyst admixing increased the head pressure with a decrease in voidance. In the case of flake-shaped supports, no large effect on pressure was seen, even though voidance also decreased. Compare Examples 12-15 with 4-8, then compare 20-21 with 2-3.

EXAMPLE 23

Figure 9:
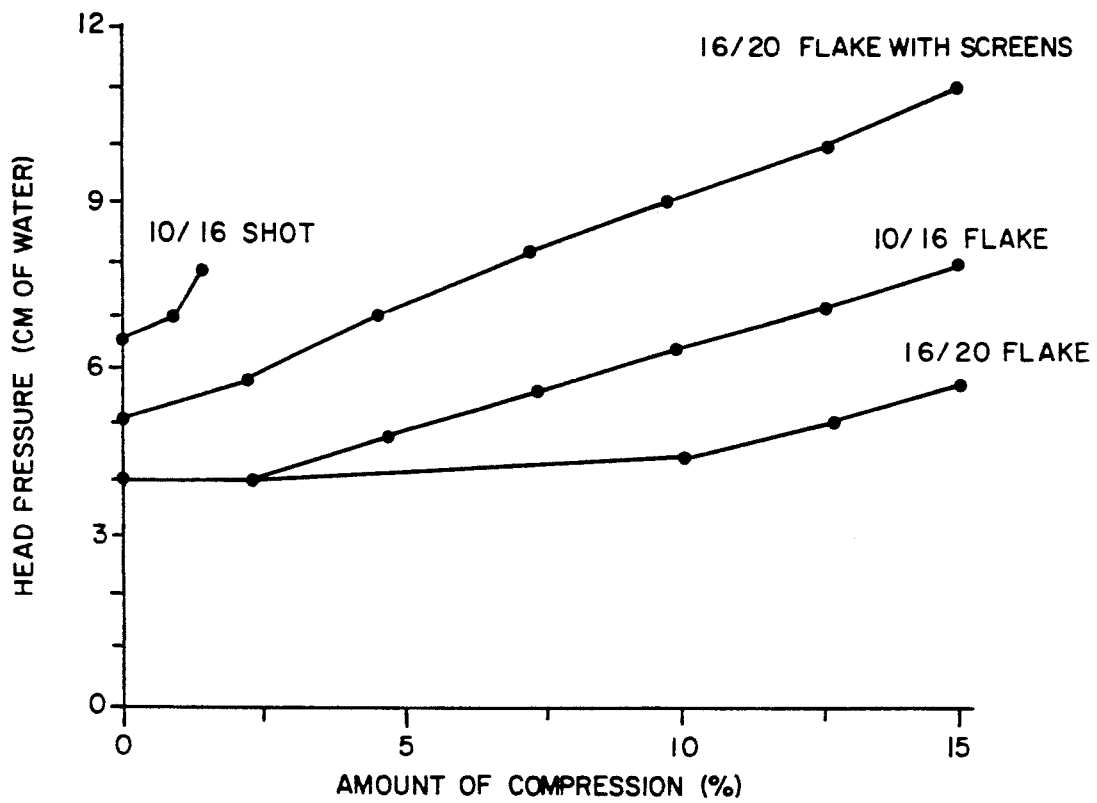
FIG. 9 is a graph of head pressure v. percentage of compression for various catalyst supports.

In this Example, a 1" I.D. pipe was used as the reactor tube. The aluminum material was added to a level of 20" in length, and a flow rate of 6.5 L/min. was passed through the system in a vertical manner at 20° C. The results of this search are plotted in the graph of FIG. 9.

When 10/16 shot was used, only about ⅜" worth of compression was possible. An increase in heat pressure was observed at a steep rate. When flake material was used, lower pressures were achieved in most cases with sizeable amounts of compression. When flaked material was sandwiched between perforated plates spaced at 1" intervals, higher pressures were realized, but so were large compression ratios. Flakes can be compressed more easily than shot since there is large voidance and they can be deformed. Shot will not yield past a certain point of compression.

EXAMPLES 24-26

These Examples investigate the use of active catalyst on an aluminum catalyst support packed within a fixed bed reactor chamber. The chamber inside measurements were 2"×18" by 20" long. The packing materials were 16/20 mesh aluminum shot and 16/20 mesh aluminum flake, both admixed with the Bi-Mo-Te-O catalyst at the 60/40 catalyst/support weight ratio, respectively. The material was packed into the block using rectangular screens as holding or perforated plates (2"×18") placed at 1" intervals along the vertical 20" length, with admixture between the screens. The reactor contents were compressed and heated to 400° C. with an inlet flow of 1.2 cfm air/propylene gaseous blend. The results are given in Table V. No channeling was observed in the catalyst beds of Examples 25 and 26. However, channeling was seen in Example 24.

TABLE V

Acrolein Yield Results Using Compressed Shot and Flake Catalyst Supports

| Ex. | Aluminum cat. support material | Head pressure, psig | Acrolein Yield, % | Remarks |
|---|---|---|---|---|
| 24 | 16/20 shot | 33 | 47 | Only a ¼" compression could be achieved (2.5%); much char was formed; hot spots seen |
| 25 | 16/20 flake | 6 | 68 | 1.25" compression used (6.3%); normal results |
| 26 | 10/16 flake | | 35 | No compression |
| " | | | 56 | Compression about 6% |
| " | | | 60 | Compression about 10% |

In Example 26, a 2" diameter aluminum tube having a length of 24" was used to explore the effect of compressing 10/16 mesh aluminum flake support containing Bi-Mo-Te-O active catalyst. The support to catalyst ratio was a series of mixtures, starting with a 30% catalyst to 70% support for the first third of the tube length, followed by a middle zone of 40% catalyst to 60% support and ending with the final third consisting of 50% catalyst and 50% support. Other catalyst loading schemes may be used, of course. The total mass filled the inside chamber and was evaluated at 410° C. Under normal flow rates of 3400 cc/min., about 35% acrolein was produced. Much unreacted propylene was also seen. When cooled, cracks in the catalyst/support bed were observed.

Next, a single compression plate was used at the top end of the bed. Compression by about 6% under the same reaction conditions gave about 56% acrolein yield. When the compression was increased to about 10%, the acrolein yield was about 60%.

The use of several plates can raise the acrolein yield to about 68%, see Example 25. One effect of using a number of plates is that the catalyst/support mixture is separated into compartments or regions by the plates.

Example 26 demonstrates that not only does compression eliminate or inhibit channeling, it also aids in increasing acrolein yield, even without perforated plates present in the catalyst bed. It is noted that the acrolein goes up from 35 to 56% upon about 5% compression and acrolein yield increases to 60% upon about 10% compression.

It may thus be seen that a catalytic fixed bed chemical reactor is provided which inhibits channelling in the catalyst bed, indeed, channeling substantially does not occur using the compression method of this invention. By "substantially" is meant that any channelling which may occur does not reduce the yield to product significantly and does not require replacement of the catalyst bed prior to the average expected lifetime of the catalyst employed. The perforated plates and the catalyst supports themselves aid in providing good temperature and reactant distribution throughout the reactor. The reactor practiced in accordance with the invention may also be operated at lower pressures than other reactors without compression or with a different catalyst support.

Many modifications may be made in the catalyst support of the present invention without departing from its spirit and scope, which are defined only in the appended claims. For example, one skilled in the art may find that certain geometric configurations of the particles, or certain alloys of the preferred metals give particularly advantageous results. From the foregoing description, it will be seen that this invention provides a catalyst support for oxidation reactions that helps achieve uniform temperature distribution throughout the catalyst bed.

We claim:

1. A fixed bed catalytic chemical reactor comprising:
   a reactor chamber for receiving a catalyst, the reactor chamber having an inlet and an outlet;
   a catalyst bed comprising deformable particulate catalyst within the reactor chamber; and
   means for compressing the catalyst bed to inhibit movement of the deformable, particulate catalyst within the catalyst bed
   where the catalyst bed has a packed, uncompressed volume and is compressed at least about 2% of the packed, uncompressed volume.

2. The fixed bed catalytic chemical reactor of claim 1 further comprising a plurality of perforated plates within the catalyst bed.

3. The fixed bed catalytic chemical reactor of claim 1 where the particulate catalyst comprises a catalyst support and an active catalyst thereon, where the catalyst support has a shape selected from the group consisting essentially of spheres, shavings, flakes, saddles, rings, cubes, prisms, pyramids, cylinders, plates, discs, helices, Intalox TM and mixtures thereof, and where the catalyst support is of a metal selected from the group consisting of aluminum, tantalum, titanium, tungsten, niobium and mixtures thereof.

4. The fixed bed catalytic chemical reactor of claim 3 where the catalyst support ranges in size between about 8 and about 40 mesh.

5. The fixed bed catalytic chemical reactor of claim 3 where the active catalyst is selected from the group consisting of a Bi-Mo-Te-O catalyst, a copper oxide catalyst, a bismuth oxide catalyst, a molybdenum oxide catalyst, an antimony oxide catalyst, a tin oxide catalyst and mixtures thereof.

6. The fixed bed catalytic chemical reactor of claim 1 where the reactor chamber has a voidance and the voidance is at least 10% of a total volume of the reactor chamber.

7. A fixed bed catalytic chemical reactor comprising:
   a tubular reactor chamber for receiving a catalyst, the tubular reactor chamber having an inlet and an outlet and a cross-section where a direction of flow through the reactor chamber is normal to the cross-section;
   a catalyst bed comprising deformable, particulate catalyst within the tubular reactor chamber;
   a plurality of perforated plates within the catalyst bed, which plates are oriented approximately parallel to the cross-section of the tubular reactor chamber; and
   means for compressing the catalyst bed to inhibit movement of the deformable, particulate catalyst within the catalyst bed
   where the catalyst bed has a packed, uncompressed volume and is compressed at least about 2% of the packed, uncompressed volume.

8. The fixed bed catalytic chemical reactor of claim 7 where each perforated plate has at least about 10 area percent of the plate surface as open perforations.

9. The fixed bed catalytic chemical reactor of claim 7 where the particulate catalyst comprises a catalyst support and an active catalyst thereon, where the catalyst support has a shape are selected from the group consisting essentially of spheres, shavings, flakes, saddles, rings, cubes, prisms, pyramids, cylinders, plates, discs, helices, Intalox and mixtures thereof, and where the catalyst support is of a metal selected from the group consisting of aluminum, tantalum, titanium, tungsten, niobium and mixtures thereof.

10. The fixed bed catalytic chemical reactor of claim 9 where the catalyst support ranges in size between about 8 and about 40 mesh.

11. The fixed bed catalytic chemical reactor of claim 9 where the active catalyst is a Bi-Mo-Te-O catalyst.

12. The fixed bed catalytic chemical reactor of claim 7 where the reactor chamber has a voidance and the voidance is at least 10% of a total volume of the reactor chamber.

13. A fixed bed catalytic chemical reactor comprising:
    a tubular reactor chamber for receiving a catalyst, the tubular reactor chamber having an inlet and an outlet and a cross-section where a direction of flow through the tubular reactor chamber is normal to the cross-section;
    a catalyst bed comprising particulate catalyst within the tubular reactor chamber, where the particulate catalyst comprises a deformable catalyst support and an active catalyst thereon, where the deformable catalyst support has a shape are selected from the group consisting essentially of spheres, shavings, flakes, saddles, rings, cubes, prisms, pyramids, cylinders, plates, discs, helices, Intalox and mixtures thereof, and where the deformable catalyst support is of a metal selected from the group consisting of aluminum, tantalum, titanium, tungsten, niobium and mixtures thereof, and where the catalyst support ranges in size between about 8 and about 40 mesh;

a plurality of perforated plates within the catalyst bed, which plates are oriented approximately parallel to the cross-section of the tubular reactor chamber; and means for compressing the catalyst bed to inhibit movement of the catalyst within the catalyst bed where the catalyst bed has a packed, uncompressed volume and is compressed at least about 2% of the packed, uncompressed volume.

14. The fixed bed catalytic chemical reactor of claim 13 where each perforated plate has at least about 10 area percent of the plate surface as open perforations.

15. The fixed bed catalytic chemical reactor of claim 13 where the active catalyst is a Bi-Mo-Te-O catalyst.

16. The fixed bed catalytic chemical reactor of claim 13 where the reactor chamber has a voidance and the voidance is at least 10% of a total volume of the reactor chamber.

* * * * *

UNITED STATES PATENT AND TRADEMARK OFFICE
CERTIFICATE OF CORRECTION

PATENT NO. : 5,262,130
DATED     : November 16, 1993
INVENTOR(S) : Charles L. Kissel and Charles M. Finley It is certified that error appears in the above-identified patent and that said Letters Patent is hereby corrected as shown below:

In col. 14, line 36, the word "Flake" should be deleted and replaced with the word --Shot--.

In col. 14, line 37, the word "flake" should be deleted and replaced with the word --shot--.

In col. 15, line 4, the word "Flake" should be deleted and replaced with the word --Shot--.

In col. 15, line 6, the word "flake" should be deleted and replaced with the word --shot--.

In col. 16, line 46, under the column entitled "Head pressure, psig" the value --3-- should be entered.

In col. 16, line 47, under the column entitled "Head pressure, psig" the value --5-- should be entered.

UNITED STATES PATENT AND TRADEMARK OFFICE
CERTIFICATE OF CORRECTION

PATENT NO. : 5,262,130
DATED : November 16, 1993
INVENTOR(S) : Charles L. Kissel, et. al.

It is certified that error appears in the above-indentified patent and that said Letters Patent is hereby corrected as shown below:

In col. 16, line 48, under the column entitled "Head pressure, psig" the value --5-- should entered.

Signed and Sealed this

First Day of November, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,262,130
DATED : November 16, 1993
INVENTOR(S) : Charles L. Kissel and Charles M. Finley

It is certified that error appears in the above-indentified patent and that said Letters Patent is hereby corrected as shown below:

On title page, item [73] Assignee: "Baker Hughes Inc., Houston, Tex." should be deleted.

Signed and Sealed this

Twenty-first Day of February, 1995

Attest:

BRUCE LEHMAN

*Attesting Officer*  *Commissioner of Patents and Trademarks*